United States Patent
Alchas

(10) Patent No.: US 7,296,566 B2
(45) Date of Patent: Nov. 20, 2007

(54) NASAL DELIVERY DEVICE INCLUDING SPRAY NOZZLE

(75) Inventor: Paul G. Alchas, Wayne, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 177 days.

(21) Appl. No.: 10/138,133

(22) Filed: May 2, 2002

(65) Prior Publication Data

US 2003/0075168 A2    Apr. 24, 2003

Related U.S. Application Data

(63) Continuation of application No. 09/417,345, filed on Oct. 14, 1999, now abandoned.

(51) Int. Cl.
*A61M 11/00*    (2006.01)
(52) U.S. Cl. .............................. 128/200.14; 128/200.22
(58) Field of Classification Search ........... 128/200.14, 128/201.18, 200.22, 203.12, 200.19, 200.21, 128/200.23, 207.18; 222/158, 153, 402.11, 222/402.13, 182, 542, 538, 562, 544, 559, 222/541; 239/482, 483, 490, 491
See application file for complete search history.

(56) References Cited

U.S. PATENT DOCUMENTS

| 3,373,743 | A |   | 3/1968  | Saffir      | 128/218 |
|-----------|---|---|---------|-------------|---------|
| 3,874,380 | A |   | 4/1975  | Baum        | 128/206 |
| 3,889,351 | A |   | 6/1975  | Tischlinger | 29/447  |
| 3,987,940 | A |   | 10/1976 | Tischlinger | 222/386 |
| 4,245,654 | A |   | 1/1981  | Raitto      | 128/765 |
| 4,344,573 | A | * | 8/1982  | De Felice   | 239/320 |
| 4,444,335 | A |   | 4/1984  | Wood et al. | 22/43   |
| 4,493,348 | A |   | 1/1985  | Lemmons     | 141/1   |
| 4,513,891 | A | * | 4/1985  | Hain et al. | 222/213 |
| 4,718,463 | A |   | 1/1988  | Jurgens, Jr. et al. | 141/11 |
| 4,767,416 | A |   | 8/1988  | Wolf et al. | 604/239 |
| 4,790,832 | A |   | 12/1988 | Lopez       | 604/283 |
| 4,801,093 | A |   | 1/1989  | Brunet et al. | 239/490 |
| 4,895,559 | A |   | 1/1990  | Shippert    | 604/15  |

(Continued)

FOREIGN PATENT DOCUMENTS

EP    0334349    3/1989

(Continued)

*Primary Examiner*—(Jackie) Tan-Uyen Ho
*Assistant Examiner*—Darwin P. Erezo
(74) *Attorney, Agent, or Firm*—David M. Fortunato; Cohen Pontani Lieberman & Pavane LLP

(57) ABSTRACT

A nasal delivery device is provided for delivering substances such as liquid drugs, vaccines and the like to a nasal passage. The nasal delivery device preferably comprises a drug container such as syringe and a separable spray nozzle. The spray nozzle includes a rigid plastic cap having a spray aperture at a distal end of the nozzle for delivering the liquid substance to the nasal passage. Attachment means is provided for attaching the spray nozzle to the syringe at the time of the delivery of the liquid substance to the nasal passage. The nozzle defines a conduit that allows fluid communication from the syringe to the spray aperture. The nozzle includes an internal valve between the spray aperture and the syringe for allowing only pressurized liquid substance to flow through the conduit and the aperture so that a mist or spray is delivered through the spray aperture.

5 Claims, 4 Drawing Sheets

U.S. PATENT DOCUMENTS

| | | | |
|---|---|---|---|
| 4,919,167 A | 4/1990 | Manska | 137/512 |
| 4,923,448 A | 5/1990 | Ennis, III | 604/239 |
| 4,929,230 A | 5/1990 | Pfleger | 604/90 |
| 4,946,069 A | 8/1990 | Fuchs | 222/43 |
| 5,064,122 A | 11/1991 | Kamishita et al. | 239/396 |
| 5,098,405 A | 3/1992 | Peterson et al. | 604/247 |
| 5,152,752 A | 10/1992 | Hammami | 604/110 |
| 5,181,658 A | 1/1993 | Behar | 239/493 |
| 5,257,726 A | 11/1993 | Graf et al. | 222/320 |
| 5,265,154 A | 11/1993 | Schotz | 379/102 |
| 5,287,983 A | 2/1994 | Reil et al. | 220/258 |
| 5,328,099 A | 7/1994 | Petit et al. | 239/372 |
| 5,373,684 A | 12/1994 | Vacca | 53/425 |
| 5,509,578 A | 4/1996 | Livingstone | 222/82 |
| 5,519,984 A | 5/1996 | Beussink et al. | 53/489 |
| 5,531,255 A | 7/1996 | Vacca | 141/285 |
| 5,537,042 A | 7/1996 | Beutler et al. | 324/432 |
| 5,597,530 A | 1/1997 | Smith et al. | 422/28 |
| 5,601,077 A | 2/1997 | Imbert | 128/200.14 |
| 5,620,425 A | 4/1997 | Heffernan et al. | 604/281 |
| 5,901,942 A * | 5/1999 | Lopez | 251/149.1 |
| 5,961,489 A | 10/1999 | Hirota | 604/94 |
| 6,041,775 A * | 3/2000 | Century | 128/200.14 |
| 6,112,743 A * | 9/2000 | Denton | 128/200.14 |
| 6,161,731 A * | 12/2000 | Sigg | 222/158 |
| 6,382,204 B1 * | 5/2002 | Jansen et al. | 128/200.19 |
| 6,530,371 B2 * | 3/2003 | Jansen et al. | 128/200.19 |
| 6,622,721 B2 * | 9/2003 | Vedrine et al. | 128/200.19 |
| 6,705,493 B1 * | 3/2004 | Mijers | 222/321.7 |
| 6,761,286 B2 * | 7/2004 | Py et al. | 222/105 |
| 6,789,750 B1 * | 9/2004 | Heldt | 239/490 |
| 7,021,561 B2 * | 4/2006 | Vedrine et al. | 239/329 |
| 7,044,125 B2 * | 5/2006 | Vedrine et al. | 128/200.19 |
| 7,182,277 B2 * | 2/2007 | Vedrine et al. | 239/329 |
| 2002/0010428 A1 * | 1/2002 | Vedrine et al. | 604/187 |
| 2002/0174865 A1 * | 11/2002 | Gatton et al. | 128/200.18 |
| 2003/0111552 A1 * | 6/2003 | Vedrine et al. | 239/329 |
| 2006/0124778 A1 * | 6/2006 | Vendrine et al. | 239/602 |
| 2006/0151629 A1 * | 7/2006 | Vedrine et al. | 239/329 |

FOREIGN PATENT DOCUMENTS

| | | |
|---|---|---|
| EP | 0 546 607 B1 | 6/1998 |
| FR | 2635084 | 9/1990 |
| FR | 2739294 | 9/1995 |
| JP | 3047521 | 1/1998 |

* cited by examiner

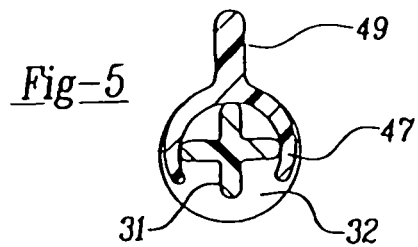
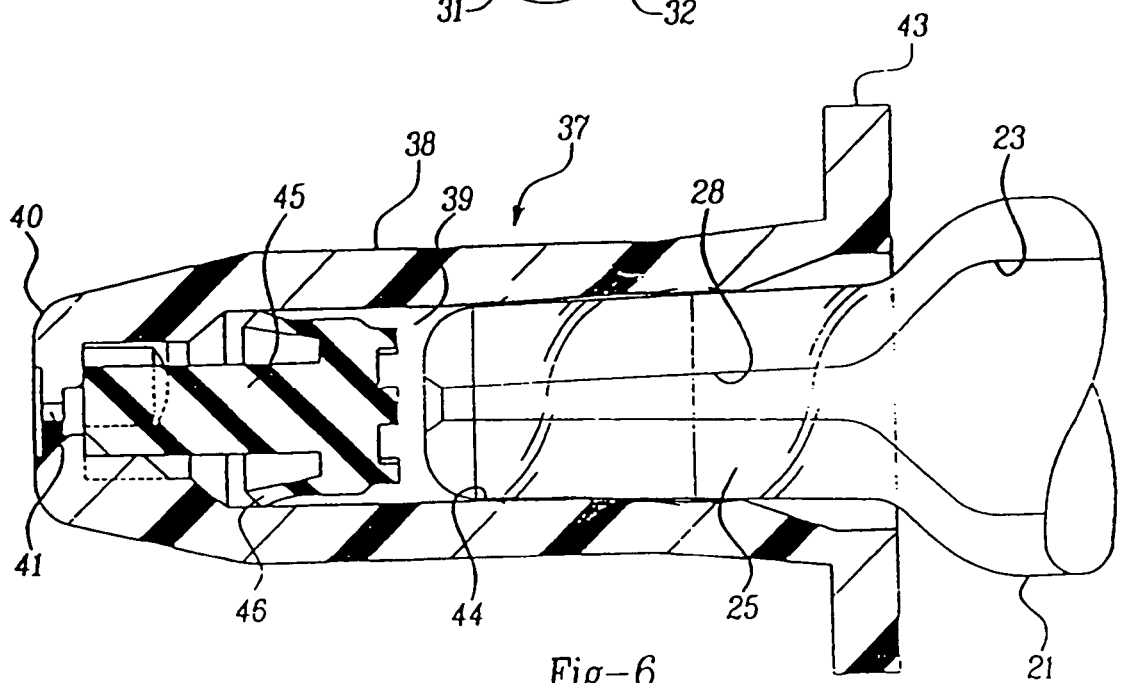
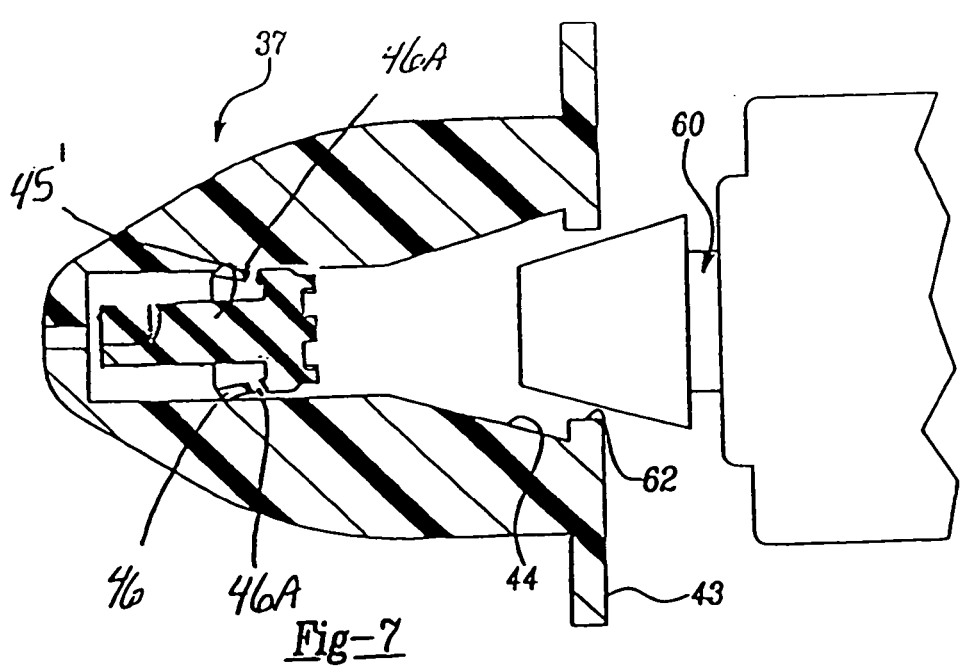

NASAL DELIVERY DEVICE INCLUDING SPRAY NOZZLE

CROSS-REFERENCE TO RELATED APPLICATIONS

This is a Continuation of U.S. application Ser. No. 09/417,345, filed on Oct. 14, 1999 now abandoned, the entire content of which is incorporated herein by reference.

FIELD OF THE INVENTION

The present invention generally relates to delivery systems for delivering substances such as drugs, vaccines and the like, and more specifically relates to a delivery device for delivering such substances intranasally, i.e., through the nose, including a spray nozzle for use with a prefilled drug container such as a syringe. In addition, the present invention relates to a nasal delivery device and more particularly to a removable spray nozzle for use with standard syringes.

BACKGROUND OF THE INVENTION

Many injectable drugs are packaged and distributed in hypodermic syringes that will eventually be used to administer the drug to the patient. The syringe is the low cost, efficient, sterile instrument of choice for delivering liquid drug through a hypodermic needle. The hypodermic syringe also can be an excellent storage device for drug placed in it by a pharmaceutical manufacturer or hospital pharmacy.

Syringes may also prove useful for distributing and administering drugs even where a hypodermic injection is not desired. Delivering a therapeutic liquid as a spray through the nasal passageway is preferred to deliver certain therapeutic liquids under certain conditions. There have been several proposed devices to make syringes useful as nasal sprayers.

U.S. Pat. No. 5,601,077 to Imbert discloses a nasal syringe sprayer for discharging the liquid contents of the syringe in a spray through the nasal passages. However, the use of that device is limited to pre-stored, liquid stable drugs. That is, the sprayer of the patent cannot be used with drugs that need to be maintained in powder or lyophilized form and reconstituted just prior to intake. Additionally, the sprayer tip of that patent does not allow an individual to load the syringe with a liquid mediation from a standard vial since the nasal spray nozzle cannot be inserted into such vials to extract the contents of the vial for loading the syringe.

U.S. Pat. No. 4,767,416 to Wolf et al. discloses a flexible, removable spray nozzle for a syringe. The spray nozzle may be attached directly to a luer fitting of a syringe or may be adapted to fit over and attached to a hypodermic needle secured to the luer fitting. In either case, the spray nozzle fits onto the syringe in order to prevent back flow and leakage of the liquid at the attachment of the spray nozzle to the syringe. One shortcoming of the device is that the nozzle does not prevent unpressurized liquid from flowing through the opening at the tip of the spray nozzle.

In view of the shortcomings and drawbacks of currently available or proposed systems, it is desirable to provide a removable spray nozzle for use with hypodermic syringes that provides a leak-free seal and prevents unpressurized liquid from flowing out the opening at the spray nozzle.

SUMMARY OF THE INVENTION

In contrast to the prior devices discussed above, it has been found that a nasal delivery device particularly suited for use in intranasally delivering substances such as drugs, vaccines and the like can be constructed in accordance with the present invention. Specifically, the invention is directed to a nasal delivery device having a removable spray nozzle adapted for delivering liquid substances such as a drug from a syringe to a nasal passage. The spray nozzle includes a plastic rigid cap having a spray aperture at one end of the nozzle for delivering the liquid substance to the nasal passage. The spray nozzle is attached to the syringe when delivery of the liquid substance will be sprayed into the nasal passage. The spray nozzle includes an internal valve that allows pressurized liquid substance to flow through the nozzle and out of the spray aperture while also preventing unpressurized liquid from flowing through the spray aperture.

In the preferred embodiment, the spray nozzle has a flange at a proximal end to prevent an individual from over-inserting the nozzle into the nasal passage. The nozzle may also include a resilient, elongate sleeve extending from the nozzle that is received over an elongate barrel of the syringe. The elongate sleeve includes a flange at an end to aid a user in grasping the assembly and delivering the liquid from the syringe to the nasal passage.

The various features and advantages of this invention will become apparent to those skilled in the art from the following detailed description of the currently preferred embodiments. The drawings that accompany the detailed description can be briefly described as follows.

BRIEF DESCRIPTION OF THE DRAWINGS

FIG. 5 is a cross-sectional view of the nasal delivery device of FIG. 2 taken along line 5-5.

FIG. 6 is an enlarged cross-sectional view of the spray nozzle of the nasal delivery device illustrating a two-component spray nozzle assembly having one-way valve features.

FIG. 7 is an enlarged cross-sectional view of the spray nozzle illustrating a snap-fit feature.

DETAILED DESCRIPTION OF THE PREFERRED EMBODIMENTS

Figure 1:
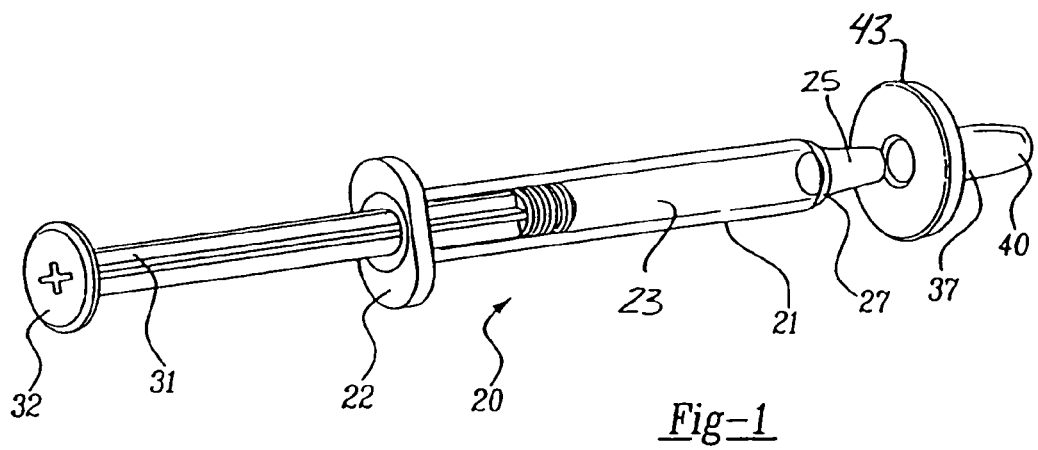
FIG. 1 is a perspective view of a nasal delivery device designed according to this invention.

FIGS. 1-6 illustrate the nasal delivery device of the present invention generally designated 20 including a drug container such as a standard syringe and a separable spray nozzle 37 attachable thereto. The syringe has an elongated barrel 21 having an open proximal end 22, a chamber 23 for retaining liquid and a tip portion 25 extending from a distal end 27 of the barrel 21. A passageway 28 extends through the tip portion 25 between the chamber 23 and an opening in the end of the tip portion.

For the purposes of this description, the term "distal end" is used to refer to the end furthest from the person holding the nasal delivery device and the term "proximal end" is meant to refer to the end closest to the holder of the nasal delivery device.

A stopper 29 is slidably positioned in fluid-tight engagement inside barrel 21 and is connected to an elongate plunger rod 31 in a conventional manner. The plunger rod 31 projects proximally from the stopper 29 and extends outwardly from the open proximal end 22 of the barrel 21. The plunger rod 31 is accessible outside of the proximal end of the barrel and is provided to move the stopper 29 along the barrel 21 to force liquid out of the chamber 23 through the passageway 28. A disc-shaped plunger rod flange 32 on the proximal end of the plunger rod 31 provides a convenient structure for applying forces to move the plunger rod 31 with respect to the barrel 21. The large surface area of the flange 32 reduces the pressure on a user's fingers while delivering the substance such as a drug, vaccine or the like through the nasal delivery device.

Figure 9:
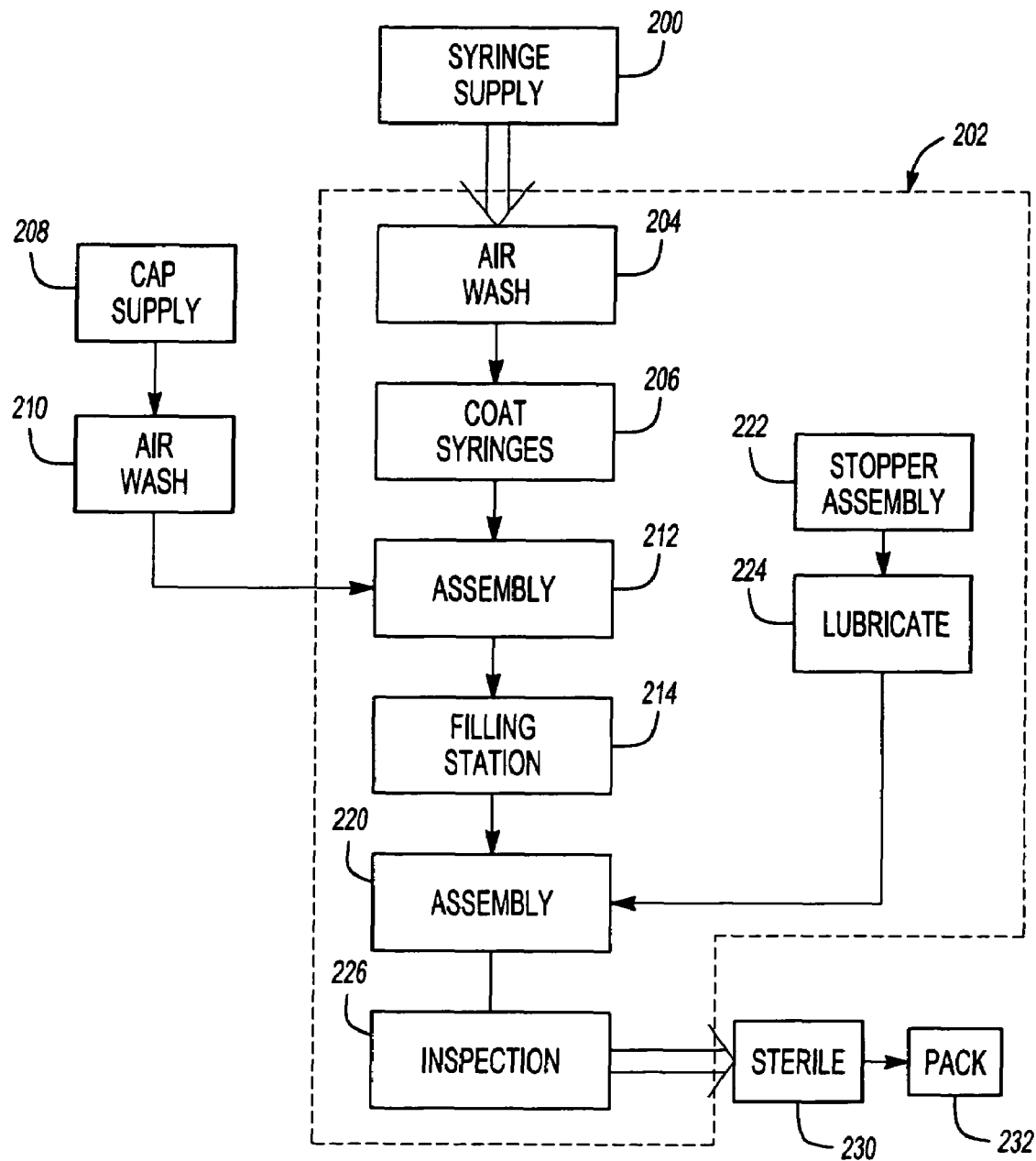
FIG. 9 is a flow chart diagram schematically illustrating a method of filling a device designed according to this invention.

A therapeutic liquid such as liquid substance 35 is contained within the chamber 23. The syringe can be prefilled or manually filled by an end user as needed. An example method of prefilling is discussed below in connection with FIG. 9. In the event that the user fills the syringe, that should be completed before the spray nozzle 37 is in place.

In order to deliver the liquid substance 35 to the nasal passage of a user, the separable spray nozzle 37 slides onto the tip 25 of the syringe 20. The internal surface of the spray nozzle 37 defines a conduit or internal passage 39 that receives the tip portion 25 and is in fluid communication with the passageway 28 when placed on the tip portion 25 of the syringe. The spray nozzle 37 also includes a distal end 40 having a spray aperture 41 in fluid communication with passage 39.

The spray nozzle 37 preferably includes two main components; a generally rigid plastic cap 38 and a generally flexible valve 45. The cap 38 preferably is constructed of a polymer, such as polypropylene, and is configured to be slidably mounted onto the tip portion 25 of the barrel 21 of the syringe. A conventional luer tip arrangement between the tip portion 25 and a cooperating opening 44 of the cap 38 secure the cap 38 in place.

A variety of cap openings and tip configurations can be used. It is useful to use tip designs that differ from conventional syringes when it is important to ensure that a standard hypodermic needle will not be used with a syringe body intended for use with the spray nozzle 37 of the present invention.

The valve 45 preferably is contained within the cap 38 between the tip portion 25 and the distal end 40 of the cap 38. The valve 45 interacts with the internal surface of cap 38 to allow only pressurized liquid to flow distally through the spray aperture 41. The valve 45 prevents unpressurized liquid in the chamber 23 from flowing through the aperture 41. Therefore, a mist of liquid rather than a stream or drops are expelled from the outlet 41.

The valve in one preferred embodiment is a skirt valve having a circumferential skirt 46 that will partially collapse or move away from the internal sidewall under the force of pressurized liquid from the chamber 23 to allow the liquid to flow from the syringe through the spray aperture 41. The skirt 46 collapses by moving away from the interior side wall of the cap 38 allowing liquid to pass through the gap, which is created by hydraulic pressure, between the skirt 46 and the cap 38. Since the skirt 46 is normally biased into engagement with the internal sidewall and only flexes in one direction, it ensures that no fluid flows in a backward direction through the cap. A wide variety of materials such as natural rubber, synthetic rubber and thermoplastic elastomers are suitable for forming the flexible valve 45 with thermoplastic elastomers being preferred.

The spray nozzle 37 preferably includes a flange 43 at a proximal end of the cap 38. Flange 43 acts as a depth limiter to prevent over-insertion of the nozzle 37 into the nasal passage.

As shown in FIG. 7, the spray nozzle 37 may be configured so that it may not be removed from the syringe. In this embodiment, the tip 25 of the syringe has a groove 60 that preferably extends circumferentially around the tip portion adjacent the syringe body. Cooperating opening 44 has a corresponding undercut 62 that forms a flange so that when the cap 38 is slid onto the tip 25, a snap-fit between the flange and groove effectively permanently secures the nozzle 37 to the syringe. The valve 45 is not illustrated in FIG. 7 for simplification. A valve preferably is included to ensure that a mist or spray is delivered into a nasal passage.

In some instances, it is useful to permit some flow back into the syringe through the spray nozzle. For example, FIG. 7 includes a modified valve 45' that has at least one passage 46a through the skirt 46. This passage allows fluid to be drawn into the syringe when using an appropriately configured vial adapter.

Figure 2:
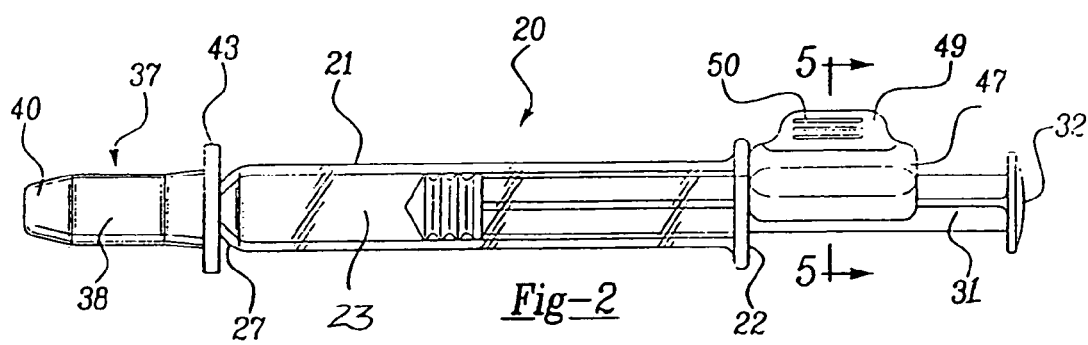
FIG. 2 is a side elevation view of the nasal delivery device of FIG. 1.
Figure 3:
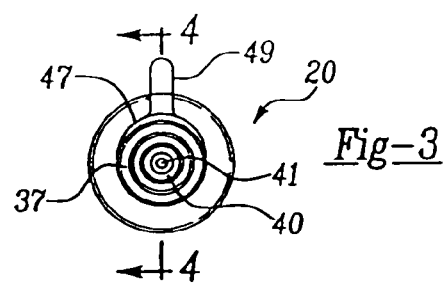
FIG. 3 is a side elevation view of the nasal delivery device of FIG. 1 viewed from the one end.
Figure 4:
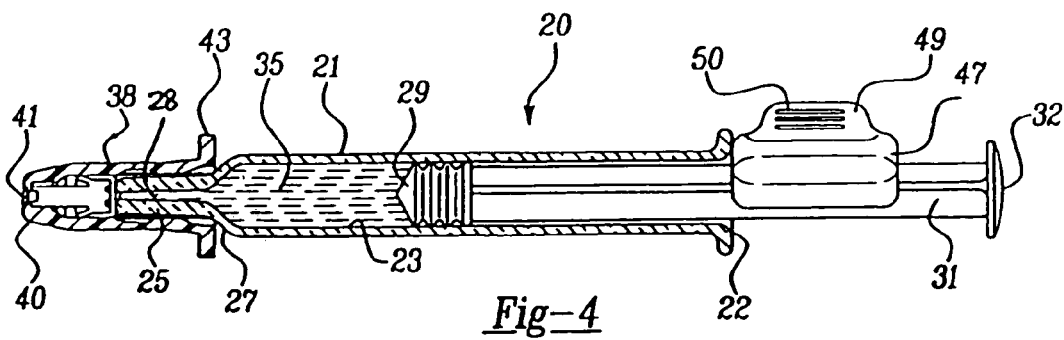
FIG. 4 is a partial cross-sectional view of the nasal delivery device of FIG. 3 taken along line 4-4.

As best seen in FIGS. 2, 4 and 5, a dosage limiter 47 can be employed. The limiter 47 partially surrounds the plunger rod 31 so that the limiter 47 will not fall off the plunger rod 31 under its own weight but may be forcibly removed from the plunger rod 31 without eliminating the ability of the nasal delivery device to deliver the substance from the chamber through the aperture 41. The limiter 47 may be designed with a thin cross-section so that it will deflect and snap over the plunger rod 31 or the plunger rod 31 may be designed to deflect under the forces of the limiter 47 during attachment or removal. Alternatively, both elements may be designed to deflect partially during installation and removal of the limiter 47. A finger tab portion 49 facilitates installation and removal. A plurality of ribs 50 provide a better grip.

The limiter 47 is adapted to interact between a radially extending projection on the plunger rod 31 such as flange 32 and proximal end 22 of the barrel 21 which includes a barrel flange 26 to limit the distal motion of the plunger rod with respect to the barrel 21. For example, the length of the limiter 47 can correspond to one-half of the volume of liquid substance in the chamber 23, which proves useful to deliver equal doses into each nostril.

In use, the nasal delivery device can be inserted into one nostril of the user while it is fully loaded such as illustrated in FIG. 4. Pressure on the plunger rod flange 22 in a distal direction (i.e., right to left according to the drawing) will cause the liquid substance 35 to flow through the passageway 28 into the conduit 39 of the cap 38, deflecting the skirt portion 46 of the flexible valve 45, and through the spray aperture 41. The plunger rod 31 can be moved until further distal motion is prevented by contact of the plunger rod flange 32 with limiter 47 which, in turn, contacts barrel flange 26. The plunger rod 31 can no longer be moved in a distal direction and approximately one-half of the liquid substance still remains in the syringe.

The user then removes the nasal delivery device from one nostril, pulls the limiter 47 off the plunger rod 31 and prepares to deliver a dose to the other nostril. With the limiter 47 now removed, the nasal delivery device may now be placed so that the spray nozzle is in the other nostril and the remaining half of the liquid substance 35 may be delivered.

Figure 8:
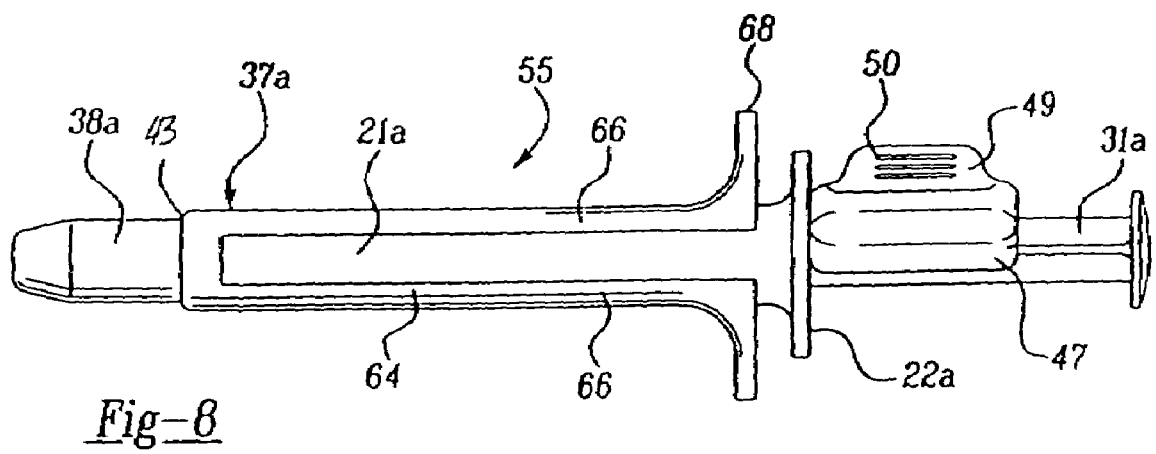
FIG. 8 is a side elevational view of an alternative embodiment of a nasal delivery device designed according to this invention.

An alternative embodiment nasal delivery device 55 is illustrated in FIG. 8. In this embodiment, the structure of the nasal delivery device is substantially similar to the nasal delivery device of the embodiment of FIGS. 1-7. Accordingly, substantially similar components that perform substantially similar functions will be numbered identically to the components of the embodiment of FIGS. 1-7 except a suffix "a" will be used to identify those components in FIG. 8.

In this alternate embodiment, the spray nozzle 37 preferably includes a generally resilient, elongate sleeve member 64 extending from the cap 38a. Elongate sleeve member 64 may be a unitary sleeve member that fully surrounds the syringe body or may include two finger-like portions 66, as shown in FIG. 8. A sleeve flange 68 provides an increased surface area to aid a user in delivering the liquid from the syringe to the nasal passage. The increased surface area is more easily retained against an individual's index and fore fingers than the typical end 22a of the syringe body. Additionally, pressure from the individual's finger serves to maintain the nozzle 37 on the syringe.

The embodiment of FIG. 8 preferably includes a valve member in the cap portion 38a as described above to ensure a spray or mist delivery. The adapter 37a can include the snap fit shown in FIG. 7.

There are several advantages provided by the present invention. The inventive arrangement having a nasal sprayer adapter can be used to deliver the substance that is targeted for nasal delivery but is not liquid-stable and, therefore, needs to be stored in powder or lyophilized form in a separate, appropriate vial. Other nasal delivery device devices that do not have a cap like that of this invention cannot accommodate such substances.

Less water vapor is lost from a syringe that works with the inventive adapter since the plastic cap need not be permanently attached to the syringe prior to use. Additionally the likelihood for pressure valve activation during plunger rod assembly and handling is lessened since the spray nozzle need not be attached to the syringe until it is ready for use. Furthermore, stability testing regarding compatibility issues is simplified since the plastic spray nozzle does not interfere with the liquid substance over a long period of time.

The advantages provided by this invention render it more useful for use with prefilled syringes. One method of pre-filling syringes to be used as a nasal delivery device is schematically shown in flow chart form in FIG. 9.

A supply of syringe barrels 200 includes the desired form of syringe, such as those illustrated and discussed above. A locally controlled environment 202 preferably is maintained in a known manner. The locally controlled environment 202 preferably is situated to immediately accept the syringes without requiring any intermediate cleaning or sterilizing steps between the supply 200 and the environment 202.

In one example, the syringe barrels are washed with air at 204 to remove any particulates from the syringes. The syringes preferably are then coated at 206 with a lubricant such as a lubricating silicone oil on the inner surface. The lubricant facilitates moving the stopper 29 and plunger rod 31 through the syringe during actual use of the device.

The end of syringes that eventually receive the spray nozzle may be capped with a tip cap within the environment 202. In one example, tip caps are supplied at 208. The tip caps are air washed at 210. The cleaned tip caps and syringe barrels are conveyed to an assembly device 212 where the tip caps are secured onto the syringes. The syringe barrel assemblies are then conveyed to a filling station 214 to be filled with the desired substance.

Once filled as desired, the stoppers 29 are inserted into the open end of the syringes at 220. Prior to inserting the stoppers 29, they preferably are assembled with the plunger rods 31 at 222 and lubricated at 224 with a conventional lubricant in a known manner. The assembled, filled syringes preferably are inspected at 226 for defects and discharged from the locally controlled environment.

The syringes typically will be sterilized at 230 and packaged at 232 into individual packages or into bulk packaging depending on the needs of a particular situation. Suitable sterilization techniques are known and will be chosen by those skilled in the art depending on the needs of a particular situation or to accommodate the properties of a given substance. Sterilizing a device designed according to this invention can be completed before or after packaging.

Variations of the filling steps are within the scope of this invention. For example, the stopper can be inserted first, then fill the syringe, followed by applying a tip cap.

The actual insertion of the desired substance can be accomplished in any of several known manners. Example filling techniques are disclosed in U.S. Pat. No. 5,620,425 to Hefferman et al.; U.S. Pat. No. 5,597,530 to Smith et al.; U.S. Pat. No. 5,537,042 to DeHaen; U.S. Pat. No. 5,531,255 to Vacca; U.S. Pat. No. 5,519,984 to Veussink et al.; U.S. Pat. No. 5,373,684 to Veussink et al.; U.S. Pat. No. 5,265,154 to Liebert et al.; U.S. Pat. No. 5,287,983 to Liebert et al.; and U.S. Pat. No. 4,718,463 to Jurgens, Jr. et al., each of which is incorporated by reference into this specification.

The description just given is exemplary rather than limiting in nature. Variations and modifications may become apparent to those skilled in the art that do no necessarily depart from the basis of this invention. The scope of legal protection given to this invention can only be determined by studying the following claims.

What is claimed is:

1. A nasal delivery device for delivering liquid substances including drug and vaccines to a nasal passage, comprising:
    a syringe having a rigid body with an outlet opening at one end;
    a separate spray nozzle including:
    a rigid cap body having an internal passage extending between an inlet opening at one end and a spray aperture at a distal end, said cap body being sealingly secured to the syringe body adjacent the outlet opening; and
    a valve having a skirt portion surrounding a base, the skirt portion movable from a first position in contact with an internal wall of the internal passage to a second position spaced from the internal wall of the internal passage when substances pressurized at or above a minimum threshold pressure flows from the inlet opening, so that only pressurized substances at or above the minimum pressure threshold level flow through the passage into and out of the spray aperture and so that substances below the minimum threshold pressure are prevented from flowing through the spray aperture, wherein the valve is configured to operate in two directions and wherein the valve defines at least one passage through the skirt portion allowing fluid to be drawn through the valve and into the syringe.

2. The device of claim 1, wherein the syringe includes a groove formed on an exterior surface near the outlet opening and the cap body includes a corresponding projection in the inlet opening that is at least partially received by the groove.

3. The device of claim 2, wherein the projection is sufficiently rigid such that the cap body is fixedly secured to the syringe when the projection is received by the groove precluding subsequent removal of the spray nozzle.

4. The device of claim 1, wherein the cap includes a radially outward projecting flange for preventing over-insertion of the nozzle into the nasal passage.

5. The device of claim 1, whereupon the syringe includes an elongated barrel that defines a chamber and said chamber prefilled with at least one substance to be nasally delivered.

* * * * *